United States Patent [19]

Jeal et al.

[11] 3,970,225

[45] July 20, 1976

[54] VALVE FOR A FLUID DISPENSER

[75] Inventors: Harvey Philip Jeal, Stevenage; David John Sheffield, Hemel Hempstead, both of England

[73] Assignee: Avdel Limited, England

[22] Filed: Dec. 20, 1974

[21] Appl. No.: 534,762

[30] Foreign Application Priority Data
Dec. 20, 1973 United Kingdom............... 59026/73

[52] U.S. Cl. .................................. 222/529; 251/9
[51] Int. Cl.² ......................................... B67C 3/28
[58] Field of Search ........... 222/105, 213, 212, 446, 222/215, 445, 103, 207, 529; 251/214, 556, 474, 7; 128/274, 231, 233

[56] References Cited
UNITED STATES PATENTS

| | | | |
|---|---|---|---|
| 2,387,923 | 10/1945 | McBrien | 222/445 |
| 2,600,631 | 6/1952 | Freedman | 222/103 |
| 2,722,933 | 11/1955 | Allen | 128/231 |

Primary Examiner—Stanley H. Tollberg
Assistant Examiner—Norman L. Stack, Jr.
Attorney, Agent, or Firm—Oblon, Fisher, Spivak, McClelland & Maier

[57] ABSTRACT

A dispenser pen for dispensing liquids such as adhesives has a tube 12 connecting a supply 14 of the liquid to a nozzle 15. The tube 12 passes between a cross-pin 19 and one end of a pivoted lever 18 which is normally urged by a spring 23 to squeeze the tube 12 between the lever and the cross-pin so as to close the tube to flow of the liquid. The region 17 of the tube between the lever 18 and the cross-pin 19 is predeformed to a generally flattened shape which can open to permit flow of liquid but can be closed with little force and by a short movement of the lever 18.

6 Claims, 3 Drawing Figures

U.S. Patent   July 20, 1976   3,970,225
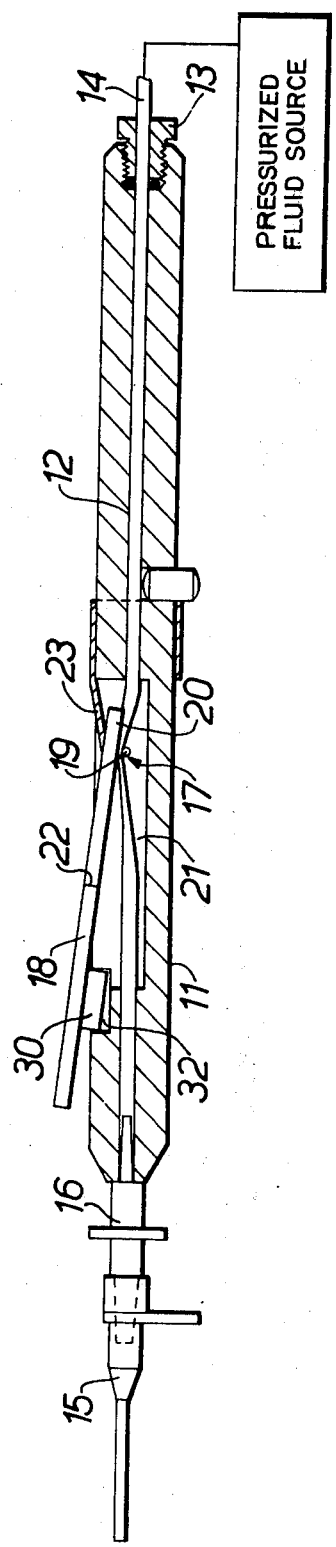
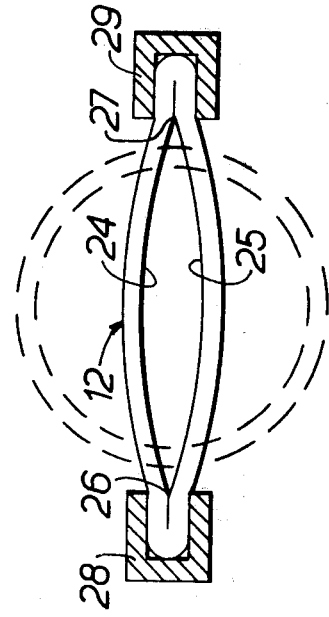
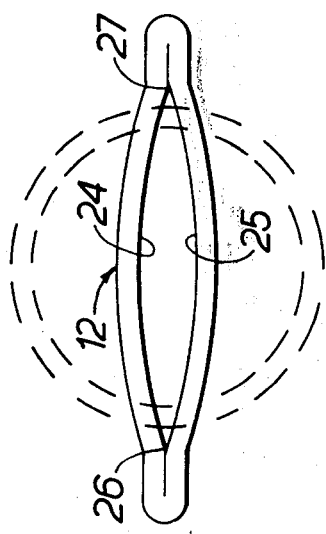

VALVE FOR A FLUID DISPENSER

The invention relates to a valve, and more particularly to a valve comprising a resiliently flexible tube through which fluid can pass and operating means for selectively squeezing the tube closed and releasing it to respectively prevent and allow passage of fluid.

The invention provides, in one of its aspects, a valve comprising a resiliently flexible tube through which fluid can pass, and operating means for selectively squeezing the tube closed and releasing it, in which the resilient tube is pre-deformed at the region where it is squeezed and released, so that when the operating means releases the tube, the tube can open to permit flow of fluid therethrough but requires relatively little squeezing by the operating means in order to reach the closed configuration.

In one application of the invention the resilient tube is of circular cross-sectional configuration except in the pre-deformed region where it is deformed to have an internal cross-sectional shape providing two opposed sides which meet each other at two spaced apart relatively sharp angled corners. The tube may be pre-deformed to a closed configuration so that, in the absence of external pressure from the operating means and of internal pressure from the fluid in the tube, the two sides are in contact. When the operating means releases the tube, the tube opens under the pressure of the fluid.

In one embodiment of the invention, the resilient tube is made of thermoplastic material and the pre-deformed configuration is obtained by applying pressure and heat to the tube at the aforesaid region thereby to give it a permanent set. The application of pressure and heat may be by squeezing the tube between two opposed heated suitably-shaped platens.

In another embodiment of the invention, the pre-deformed configuration of the resilient tube is obtained by applying clamps to opposite edge portions of the tube at the aforesaid region.

Two specific embodiments of the invention will now be described by way of example and with reference to the accompanying drawings, in which:

FIG. 1 is a longitudinal axial cross-section through an adhesive dispenser pen incorporating a valve according to either embodiment of the invention; and FIGS. 2 and 3 are transverse cross-sections through the tube at its pre-deformed region when open under the pressure of fluid in the two embodiments respectively.

The adhesive dispenser pen shown in FIG. 1 comprises a tubular body 11 having an axial bore through which extends a tube 12 of resilient polytetrafluroethylene (PTFE) material. One end of the tube is connected by means of a coupling 13 to a supply pipe 14 along which a liquid adhesive (e.g. an anaerobically curable or cyanoacrylate adhesive) is supplied under pressure, the fluid pressure supply source being shown at 14'. The adhesive passes along the tube 12 to the other end and then out through a narrow-ended nozzle 15 which is connected to the said other end of the tube 12 by a connector 16. Passage of the adhesive along the tube 12 is normally prevented by the tube being squeezed closed at a region 17 about mid-way along its length. At this position the tube is squeezed between an operating member in the form of a lever 18 and a cross-pin 19. The wall of the body is provided with an aperture in the form of an elongate slot 21 which communicates between the bore and the exterior of the body at a position spaced from the ends of the body, the bore being slightly enlarged in the region where it is intersected by the slot. The cross pin 19 is secured diametrically across the enlargement in the bore of the tubular body 11. The lever 18 is in the form of an elongate strip having an inner end portion 20 of reduced width within the slot and an outer end portion providing shoulders 22 on which the lever pivots against the outer surface of the body 11. The inner end 20 of the lever is spring-urged, by means of a spring 23, towards the pin 19, thus tending to squeeze the tube 12 flat.

The lever 18 lies at an angle to the external surface of the body 12, and the wider part of the lever, which projects from the slot 21, is provided with a locating button 30 which engages in a locating recess 32 in the wall of the body 11.

The valve is opened by depressing the outer end of the lever 18 towards the body, thus pivotally moving the lever and withdrawing the inner end 20 from the pin 19 and allowing the tube 12 to open under the pressure of adhesive from the supply 14.

As indicated, the resilient tube 12 is pre-deformed at the region where it passes between the lever 18 and the pin 19. FIGS. 2 and 3 show two alternative embodiments of this region of the tube.

In FIG. 2, the tube is formed of thermoplastic material and has been given a permanent set by applying heat and pressure to it. This is done using two opposed heated platens of suitable size and shape, between which the appropriate region of the tube is squeezed for a suitable time. The pre-deformed shape, in the absence of any external force on the tube, is with the walls of the tube completely flattened together. FIG. 2 shows the cross-sectional shape of the tube opened under pressure from the fluid when the operating means releases the tube. The shape comprises two sides 24, 25 which meet each other at two spaced-apart, relatively sharp angled corners 26, 27. It should be noted that beyond each corner 26, 27, the inner surface of the wall of the tube does not separate to form a bight, which tends to happen if a similar non-predeformed tube of normally circular cross-section is temporarily squeezed together, between the lever 18 and the pin 19, to close it. Such bights are formed due to the resistance of the tube against being bent about the small radius into which the tube wall is constrained to bend at each end of its cross-section. It is believed that these bights, if allowed to form, tend to allow leakage when the valve is in the "closed" position. By predeforming the tube so that the opposed sides 24, 25 maintain close contact with each other in the corner regions where they join, the formation of bights through which liquid might flow, even when the tube has been squeezed in an attempt to close it, is avoided.

In FIG. 3, a similar pre-deformed, generally flattened configuration of the tube 12 is obtained by means of two small clamps 28, 29 applied to opposite edge portions of the tube at the region 21. The size and strength of the clamps are such that they hold each edge portion of the tube folded together with a force much greater than that which could be available in practice between the inner end of the lever 18 and the cross pin 19.

It will be appreciated that the deformation of the tube results in the deformed region having an internal cross-sectional area less than that of the undeformed tube. However in both embodiments, the cross-sectional area of the tube 12 at the region 21 may be much greater than suggested by FIGS. 2 and 3. It may be as much as 70% of the area of the circular undistorted tube, which is shown in broken lines in FIGS. 2 and 3 for comparison. However the cross-sectional area of the tube at the region 21, when in the open position, need only be enough so as not to restrict flow through the nozzle 16, which is of relatively small cross-sectional area.

A short movement of the inner end 20 of the lever 18 is sufficient to open or close the deformed region of the tube to permit or arrest flow of liquid, and little force if is required to close the deformed portion compared with the force required to close the underformed tube.

The invention is not restricted to the details of the foregoing example.

We claim:

1. A valve comprising:
   a flexible tube of resilient material, said tube normally resiliently assuming a shape providing an open bore through which fluid can pass, said open bore having a cross-sectional shape which is continuously curved; and
   operating means for selectively squeezing a region of the tube in order to close said bore and for releasing said region of said tube in order to allow the bore to open,
   said region of said tube which is squeezed and released having two diametrically opposed longitudinal folds whereby the cross sectional shape of said bore within said region is deformed so as to present two opposing sides which meet each other at sharply angled corners located within said folds,
   whereby the force required to squeeze said opposing sides together and close said bore within said region is less than the force required to close said bore within the remainder of said tube.

2. A valve according to claim 1, wherein:
   said tube is made of a thermoplastic material within which said longitudinal folds are permanently set.

3. A valve according to claim 1 wherein:
   clamps are disposed upon said tube and within said region so as to maintain said longitudinal folds within said tube.

4. A valve according to claim 1, wherein the operating means comprises a pivotally movable lever, said lever being normally urged to squeeze the region of the tube to a closed condition.

5. A valve according to claim 4, wherein a pin cooperates with the lever, said pin extending transversely across the tube whereby the tube may be squeezed between the lever and the pin along a line of contact across the tube.

6. A valve according to claim 1, wherein:
   one end of said valve is connected to a source of liquid supply and the other end of said valve is connected to a narrow-ended nozzle for dispensing the liquid.

* * * * *

UNITED STATES PATENT AND TRADEMARK OFFICE
CERTIFICATE OF CORRECTION

PATENT NO. : 3,970,225
DATED : July 20, 1976
INVENTOR(S) : Harvey Philip Jeal et al It is certified that error appears in the above-identified patent and that said Letters Patent are hereby corrected as shown below:

[73] delete "Avdel Limited, England" and insert therefor -- Aerpat A.G. Zug, Switzerland --.

Signed and Sealed this

Twenty-first Day of September 1976

[SEAL]

Attest:

RUTH C. MASON
Attesting Officer

C. MARSHALL DANN
Commissioner of Patents and Trademarks